United States Patent [19]

Stem et al.

[11] Patent Number: 4,855,529
[45] Date of Patent: Aug. 8, 1989

[54] ISOMERIZATION PROCESS WITH PRELIMINARY NORMAL PARAFFIN AND MONO-METHYL PARAFFIN FEED CAPTURE STEP

[75] Inventors: Stephen C. Stem; Wayne E. Evans, both of Houston, Tex.

[73] Assignee: Shell Oil Company, Houston, Tex.

[21] Appl. No.: 185,740

[22] Filed: Apr. 25, 1988

[51] Int. Cl.$^4$ .............................................. C07C 5/27
[52] U.S. Cl. ...................... 585/737; 585/738; 585/739; 585/820; 585/821; 585/822; 208/310 R; 208/310 Z
[58] Field of Search ................... 208/310 Z, 134, 141, 208/310 R; 585/737, 734, 735, 738, 820, 821, 822, 739

[56] References Cited

U.S. PATENT DOCUMENTS

| | | | |
|---|---|---|---|
| 2,956,089 | 10/1960 | Mattox et al. | 585/738 |
| 3,755,144 | 8/1973 | Asselin | 208/95 |
| 3,836,455 | 9/1974 | Blytas | 208/310 |
| 4,016,245 | 4/1977 | Plank et al. | 423/328 |
| 4,176,053 | 11/1979 | Holcombe | 208/310 |
| 4,191,845 | 3/1980 | Rubin et al. | 585/737 |
| 4,210,771 | 7/1980 | Holcombe | 585/701 |
| 4,251,499 | 2/1981 | Nanne et al. | 423/329 |
| 4,440,871 | 4/1984 | Lok et al. | 502/214 |
| 4,476,345 | 10/1984 | Gray et al. | 585/820 |
| 4,654,138 | 3/1987 | Derouane et al. | 208/114 |
| 4,709,117 | 11/1987 | Gray, Jr. | 585/738 |
| 4,717,784 | 1/1988 | Stem et al. | 585/822 |

FOREIGN PATENT DOCUMENTS

0209997 1/1987 European Pat. Off. .............. 208/18
0876730 8/1959 United Kingdom ................ 585/738

Primary Examiner—Anthony McFarlane
Attorney, Agent, or Firm—Kimbley L. Muller

[57] ABSTRACT

This invention relates to a process for increasing the octane of a refinery gasoline pool by segregating components which are increased in value by isomerization from those which are diminished in octane value by isomerization. The preferred feed stream of this process comprises di-branched paraffins, mono-methyl-branched paraffins and normal paraffins from which mono-methyl-branched and normal paraffins are selectively captured by a shape-selective molecular sieve. The preferred separatory shape-selective molecular sieve has a pore size of 5.5×5.5 to 4.5×4.5A but excluding 4.5×4.5A. Mono-methyl-branched paraffins and normal paraffins are removed from the shape-selective molecular sieve and isomerized in an isomerization zone to form di-methyl branched paraffins. An isomerization zone effluent stream is produced comprising unisomerized normal paraffins, mono-methyl-branched paraffins and di-branched paraffins. It is within the scope of this invention for the isomerization zone effluent stream (isomerate) to undergo further separation wherein a recycle stream is generated comprising normal paraffins or normal paraffins and mono-methyl-branched paraffins which can be returned to the isomerization zone. The isomerization zone effluent stream is separated by means of a calcium 5A aluminosilicate, a ferrierite aluminosilicate or a combination thereof.

46 Claims, 5 Drawing Sheets

ISOMERIZATION PROCESS WITH PRELIMINARY NORMAL PARAFFIN AND MONO-METHYL PARAFFIN FEED CAPTURE STEP

FIELD OF THE INVENTION

This invention relates to a process which ultimately enhances the octane of a refinery gasoline pool. The octane is increased by the use of a select feed pretreatment preceding isomerization. This select pretreatment enables the segregation of said feed into a portion which is increased in value by isomerization from that portion which would be diminished in value by isomerization. This segregation ultimately results in a greater proportion of di-methyl-branched paraffins in the refinery gasoline pool while reducing the proportion of mono-methyl-branched paraffins. As a corollary, the field of this invention is concerned with the development of a pre-isomerization sieve to preserve high octane products while maximizing the quantity of normal and mono-methyl-branched paraffins which are subject to isomerization.

As a result of pollution and environmental problems, retail gasolines in the United States eventually will have a phase-down lead content. Maintenance of high octane gasolines by methods other than lead addition is of continuing interest to U.S. refiners. Two major techniques are available to acquire high octane gasoline pools without lead addition. First, hydrocarbons can be reformed in the presence of a reforming catalyst, such as a platinum rhenium catalyst, to a high octane gasoline. Second, normal paraffins can be isomerized to branched paraffins which possess higher octane qualities. This invention concerns the latter of these two processes and is an improvement over standard isomerization processes. The process of this invention supplies a unique pre-isomerization separation step to maximize the effectiveness of the isomerization while preserving that portion of the feed stream which would be diminished in value by isomerization. This is accomplished without the expense of additional hydrocarbon consumption.

From the standpoint of increasing octane, it is desirable that hydrocarbons in gasoline have maximum branching. For example, methylpentanes have lower octane ratings than do dimethylbutanes, thus in an isomerization process it is beneficial to maximize the content of dimethylbutanes (di-branched paraffins) at the expense of methyl-pentanes (mono-methyl-paraffins). Applicants have discovered that a means to accomplish this goal is to formulate and develop an ideal pre-isomerization separation step using a particular shape selective molecular sieve. The overall combined product stream of this isomerization process contains an increased amount of dimethylbutanes, the most highly branched and highest octane of the $C_6$ saturates. This results in a direct octane enhancement to the resultant gasoline blending pool. In refineries which restrict production of gasoline due to octane limitations, this octane enhancement can permit increased gasoline production as well.

BACKGROUND OF THE INVENTION

Pertinent areas of the classification manual concerned with this type of invention are, among others, Class 208, Subclass 310 and Class 585, Subclasses 820, 701 and 738.

In Gray Jr. et al, U.S. Pat. No. 4,476,345, an invention is disclosed in which a portion of one of the product streams in an isomerization process is used to wash a recycle gas stream to improve the quality of the isomerate products. The molecular sieve adsorbent of Gray is one which can be naturally occurring or synthetically produced comprising a three-dimensional crystalline-zeolitic aluminosilicate which will selectively, on the basis of molecular size of the pores, adsorb normal paraffins from the isomerized product from branched chained and/or cyclic paraffins. The molecular sieves have pore diameters of about 5A and are exemplified by a calcium 5A zeolite which exhibits pore diameters ranging from about 3 to about 5 Angstroms.

The Gray et al disclosure is an improvement upon an isomerization process as taught in Holcombe, U.S. Pat. No. 4,210,771. This is a process for the virtual complete isomerization of normal paraffin hydrocarbons in a feed stream consisting essentially of mixed normal and branched hydrocarbons, where the feed stream is passed first through an isomerization reactor and the products derived therefrom are passed to an adsorption section which separates normal from branched paraffins to form an isomerate having both di- and mono-branched paraffins. A recycle stream comprising nearly pure normal paraffins is usually recycled to exhaustion. Other disclosures which may be commensurate with Holcombe comprise U.K. Pat. No. 876,730 and U.S. Pat. No. 3,755,144 issued to Asselin.

The zeolite molecular sieve employed in Gray et al and Holcombe may be selected from any adsorbent which selectively adsorbs normal paraffins based on the molecular pore size of the aluminosilicate. Particularly suitable zeolites of this type are calcium exchanged zeolite 5-A. Naturally occurring zeolite molecular sieve which could be substituted for calcium 5-A zeolite include chabazite and erionite. The particular flow scheme of adsorption as taught by Holcombe '771 is herein incorporated by reference to show an operable multiple zeolitic molecular sieve adsorption means, to achieve proper adsorption-fill and desorption-purge. The Holcombe patent is completely silent as to arrangements of a multiple number of different sieves which may be present in the absorption separation technique. In fact, in the drawing of Holcombe, the adsorption bed systems, 44, 46, 48, and 50, are all comprised of calcium 5A zeolite in the form of 1/16-inch cylindrical pellets. Branched paraffins, whether they be mono- or di-branched, flow through the adsorption bed while unbranched normal paraffins are adsorbed. After a purge of the adsorbed normal paraffins from the zeolite molecular sieve, the recycle stream is comprised nearly entirely of normal paraffins and recycle hydrogen. This is mixed with the incoming feed before charge to the isomerization zone. The placement of these types of molecular sieves upstream of isomerization will result in only normal paraffins being passed to the isomerization zone while mono-methyl-branched paraffins, in admixture with the more desirable di-branched paraffins, will not be captured and, therefore, will not be further isomerized into the more valuable di-branched paraffins.

A second Holcombe patent, U.S. Pat. No. 4,176,053, discusses a normal paraffin-isomerization separation process. By this technique, normal paraffins are isolated from a feedstock mixture comprising normal and branched paraffins at super atmospheric pressures using an adsorption system comprising at least four fixed adsorbent beds containing a calcium 5A molecular sieve. A stream is formed comprising vapor from void space purgings of the adsorbent and feedstock containing iso-paraffins and normal paraffins. The molecular sieve employed to separate normal paraffins from said stream is selected to adsorb only normal paraffins from a mixture of branched, cyclic and normal hydrocarbons.

In U.S. Pat. No. 3,836,455 issued to Blytas, the separation of methylpentane and 2,2-dimethylbutane (as contrasted with 2,3-dimethylbutane of the instant invention) is accomplished using an offretite zeolite. U.S. Pat. No. 4,251,499 issued to Nanne et al teaches that ferrierite sieves are effective for dividing substantially unbranched structures (n-paraffins) from mixtures of same with branched structures (both mono-methyl and di-branched paraffins). Such was the state of the art in 1981 although the instant invention has shown that this teaching is no longer accurate in regard to the adsorption capacity of ferrierite aluminosilicates as defined herein.

These patents teach that it is most advantageous to recycle normal paraffins to thereby isomerize the same to the isomerate components comprising mono-methyl-branched paraffins and di-branched paraffins. These disclosures suggest that the isomerate will have a certain quantity of mono-methyl-branched paraffins derived from the isomerization zone. These mono-methyl-branched paraffins will have an inherently lower octane value than the di-branched paraffins whether or not they are mixed with the more preferred di-branched paraffins before or after isomerization.

In contrast, applicants have discovered a new and more efficient isomerization process utilizing a pre-isomerization molecular sieve whereby both normal paraffins and mono-methyl-branched paraffins are passed to isomerization with little or no presence of di-branched paraffins. Using the specific pre-isomerization molecular sieve separation technique of this process, mono-methyl-branched paraffins are diminished in the refinery gasoline pool while di-branched paraffins are both preserved and produced. In other words, this process increases the degree of branching in the ultimate refinery gasoline pool by improving the effectiveness of the isomerization step

OBJECTS AND EMBODIMENTS OF THE INVENTION

An object of this invention is to provide a unique isomerization process which will preserve the alrady high octane quality of select constituents of the feed prior to conversion of the other remaining paraffinic material to high octane quality isomerate.

Another object of this invention is to provide a unique separatory sieve placement to pretreat an isomerization zone feed stream to preserve (before isomerization) constituents within said feed, such as aromatics, naphthenes, and di-branched paraffins, which would be diminished in value if they were passed to isomerization.

Another object of this invention is to provide a unique isomerization process whereby a feed stream to an isomerization zone will contain both normal and mono-methyl-branched paraffins, wherein the normal paraffins are isomerized to mono-methyl-branched paraffins and wherein the mono-methyl-branched paraffins are isomerized to di-methyl-branched paraffins.

Another object of this invention is to provide a unique preliminary sieve step to an isomerization process to insure maximum conversion to the di-branched paraffin from normal and mono-methyl paraffins in the isomerization zone.

Yet another object of this invention is to provide a process step whereby 2,3-dimethylbutane can be removed from a mixture containing 2,3-dimethylbutane, normal hexane, and mixtures of methyl pentanes to segregate the 2,3-di-branched paraffins while allowing the normal hexane and methyl pentanes to be isomerized to methyl pentanes and 2,3-dimethylbutane.

One embodiment of this invention resides in a process for the isomerization of paraffins from a mixed hydrocarbon stream comprised of normal paraffins, mono-methyl-branched paraffins, di-methyl-branched paraffins, said process comprising the steps of passing said mixed hydrocarbon stream to a feed separation zone comprising a shape-selective separator molecular sieve having a pore size intermediate $5.5 \times 5.5$ to $4.5 \times 4.5 A$ and excluding $4.5 \times 4.5 A$, said pore size being sufficient to permit entry of said normal paraffins and said mono-methyl-branched paraffins but restrictive to prohibit entry of di-branched paraffins, separating, in said feed separation zone, at first separation conditions, by means of said shape-selective separatory sieve, said di-branched paraffins from said normal paraffins and mono-methyl- branched paraffins, recovering from said feed separation zone a feed separation zone effluent comprising said di-branched paraffins, recovering from said separation zone an isomerization feed stream comprising said normal paraffins and said mono-methyl-branched paraffins and passing at least a portion of said isomerization feed stream to an isomerization zone maintained to isomerization conditions and containing an isomerization catalyst to produce an isomerization zone effluent stream comprising di-branched paraffins, mono-methyl-branched paraffins and normal paraffins.

Another embodiment of this invention resides in a process for the preparation of an isomerate from a hydrocarbon feed stream mixture containing normal hexane, methyl pentanes and di-methyl butane which comprises passing said feed stream to a feed separation zone containing a separatory shape-selective molecular sieve having a pore size intermediate $5.5 \times 5.5$ to $4.5 \times 4.5 A$ and excluding $4.5 \times 4.5 A$, said shape-selective molecular sieve being effective to permit entry of said normal hexane and said mono-methylpentanes and restrictive to prohibit entry of said dimethyl butane and to thereby separate said dimethyl butane from said normal hexane and mono-methylpentanes, recovering said dimethyl butanes as a feed separation zone effluent and recovering said adsorbed normal hexane and monomethylpentanes and passing said normal hexane and mono-methylpentane to an isomerization zone and isomerizing, at isomerization conditions, in the presence of an isomerization catalyst said normal hexane to methyl pentanes and dimethyl butane and isomerizing said monomethylpentanes to dimethyl butane, and to form an isomerization effluent isomerate stream comprising unisomerized normal hexane, mono-methylpentanes and dimethyl butane.

BRIEF DESCRIPTION OF THE INVENTION

This invention is concerned with the novel use of a select adsorbent molecular sieve having particular separatory qualities to treat a feed stream to an isomerization process to preserve those constituents in the feed which would be diminished in value by isomerization while at the same time providing to isomerization a constituent (mono-methyl-branched paraffins) which was unattainable with prior art processes. It is preferred that the separatory sieve is a molecular sieve having a pore size of 5.5×5.5 to 4.5×4.5A and being selective to permit adsorption of mono-methyl-branched paraffins and normal paraffins. This sieve is sized to be restrictive to the adsorption of di-branched paraffins in addition to any aromatics or naphthenes which may be present in the feed stream along with the paraffinic components.

DETAILED DESCRIPTION OF THE INVENTION

The schematic process flow of this invention exemplified by FIGS. 2 through 5 of the drawings is initiated by the novel separatory treatment of the hydrocarbon feed material prior to isomerization. Contemplated feed streams to this isomerization process are comprised mainly of isomeric forms of saturated hydrocarbons having $C_6$ or greater carbon atoms. In order to take full advantage of the highlights of this invention, the feed material should contain an amount of di-branched paraffinic hydrocarbons which are known for their high octane value worthy of separation. The feed stream can comprise normal paraffins, mono-methyl paraffins and dimethyl paraffins. The carbon numbers of these paraffins are preferably $C_6$ or higher for the normal paraffins, mono-methyl-branched paraffins and di-branched paraffins. These feedstocks are usually derived from refinery operations and can contain quantities of $C_5^-$, $C_7^+$, and cyclic paraffins. Olefinic and aromatic hydrocarbons may also be present. When naphthenes and aromatics are present, they will not be adsorbed by the sieve upstream of isomerization and will pass with the dimethyl paraffins. This is very advantageous due to the relatively high octane quality of some of the aromatic and naphthenic material derived from this separation. The preferred feedstocks will contain more than 25 mole percent normal hexane. By use of the process of this invention, the actual hydrocarbon feed stream to the isomerization zone will contain both normal paraffins and mono-methyl paraffins in contrast to other prior art techniques using a calcium 5A sieve to treat a feed stream which passes only the normal paraffins to isomerization.

The molecular sieves of this invention have precise pore dimensions intermediate the channel pore dimensions present in either a calcium-5A sieve or a ZSM-5 sieve. The particular molecular sieve of this invention is capable of adsorbing not only normal hexane but also methylpentanes as well. The preferred molecular sieve has eight and ten member rings and pore dimensions intermediate 5.5×5.5 and 4.5×4.5A, but excluding 4.5×4.5A (i.e., calcium 5A) Angstroms.

The preferred molecular sieve of this invention is ferrierite. This aluminosilicate exhibits a greatly increased adsorption capacity towards methylpentane relative to a calcium-5A molecular sieve, even if the latter is used upstream of isomerization. It has been discovered that both the sodium and the hydrogen forms of the ferrierite are viable although it is preferred that the ferrierite be utilized with a cation of an alkali metal, or alkaline earth metal or transition metal cation. The molecular sieves of this invention include ferrierite and other analogous shape-selected materials with channel dimensions intermediate those of the calcium-5A and ZSM-5 molecular sieves. Other examples of crystalline sieves will include aluminophosphates, silicoaluminophosphates, and borosilicates.

Exemplary of the wide range of aluminophosphates available in the prior art are the following articles:
(1) Synthesis and properties of several aluminophosphate molecular sieves
   Quinhua, Xu; Dong, Jialu; Yan, Aizhen; Jin, Changtai
   Dep. Chem., Nanjing Univ.
   Nanjing, Peopl. Rep. China
   Acta Phys. Chem., 31(1-2), 99-108
   66-3 (Surface chemistry and Colloids)
(2) Synthesis of aluminophosphate molecular sieve A1P04-12
   Xu, Wen Yang; Guo, Chang Jie; Do. Tao
   Shanxi, Peopl. Rep. China
   J. Inclusion Pheno., 4(4), 325-31
   66-63 (Surface Chemistry and Colloids)
(3) Synthesis and properties of new aluminophosphate molecular sieves CNU-n (n=1,2,3)
   Xu, Qinhua; dong, Jialu; Yan, Aizhen; Jin, Changtai
   Dep. Chem., Nanjing Univ.
   Nanjing, Peopl. Rep. China
   Wuji Huaxue, 1, 74-80
(4) Structural features of aluminophosphate materials with aluminum/phophorus=1
   Bennett, J. M.; Dytrych, W. J.; Pluth, J. J.; Richardson, J. W., Jr.; Smith, J. V.
   Inorganic Chemicals and Reactions 78-5
   Union Carbide Corp.
   Tarrytown, NY 10591, USA
(5) Zeolites, (5), 349-60
   75-0 (Crystallography and Liquid Crystals)
   The structure of coprecipitated aluminophosphate catalyst supports
   Cheung, T.T.P.; Willcox, K. W.; McDaniel, M. P.; Richardson, Johnson, M. M.; Bronnimann, C.; Frye, J. Phillips, Res. Cebt,
   Bartlesville, OK 74004, USA
   J. Catal., 102(1), 10-20
   67-1 (Catalysis, Reaction Kinetics, and Inorganic Reaction Mechanisms)
(6) Site energy distribution and catalytic properties of microporous crystalline A1P04-5
   Choudhary, Vasant R.; Akolekar, Deepak B.
   Chem. Eng. Div., Natl. Chem. Lab.
   Pune 411 008, India
   J. Catal., 103(1), 115-25
   51-6 (Fossil Fuels, Derivatives, and Related Products)

The silicoaluminophosphate sieves are described in U.S. Pat. Nos. 4,440,871 and 4,654,138, all of the teachings of which are herein incorporated by references. In addition, European Pat. No. 209,997 discloses the use of silicoaluminophosphates for catalytic dewaxing of lube oils. Other technical articles discussing the structure of these select molecular sieves are as follows:
(1) Structure of an aluminosilicophosphate
   Ito, Masatoki, Shimoyama, Yumiko; Saito, Yoshihikl; Tsurita, Ysaushi; Otake, Masayuki
   Fac. Sci, Technol., Keio Univ.
   Yokohama 223, Japan
   Acta Crystallogr., Sect. C: Cryst. Struct. Commun., C41(12), 1698-700
   75-8 (Crystallography and Liquid Crystals)
(2) Adsorption properties of microporous aluminophosphate (A1P04-5)
   Stach, H.; Thamm, H.; Fiedler, K.; Grauert, B.; Wieker, W.; Jahn, E.; Oehlmann, G.

Cent. Inst. Phys. Chem., Acad. Sci. GDR
Berlin-Adlershof 1199, Germ. Dem. Rep.
Stud. Surf. Sci. Catal., 28 (New Dev. Zeolite Sci. Technol.), 539-6
66-3 (Surface Chemistry and Colloids)
(3) Molecular sieve effects in carboniogenic reactions catalyzed by silioaluminophosphate molecular sieves
Pellet, R. J.; Long, G. N.; Rabo, J. A.
Union Carbide Corp.
Tarrytown, NY 10591, USA
Stud. Surf. Sci. Catal., 28 (New Dev. Zeolite Sci. Technol.), 843-9 45-4
(Industrial Organic Chemicals, Leather, Fats, and Waxes)
(4) Methanol conversion to light olefins over silicoaluminophosphate molecular sieves
Kaiser, Steven W.
Union Carbide Corp.
South Charleston, WV 25303, USAArabian J. Sci. Eng., 10(4), 361-6 35-2 (Chemistry of Synthetic High Polymers) 23, 45
(5) Synthesis of aluminosilicophosphate molecular sieves and their adsorption-structural properties
Pechkovskii, V. V.; Margulets, A. V.; Eschchenko, L. S.
BTI
USSR
Khim. Khim. Tekhnol. (Minsk), 20, 46-50 78-4 (Inorganic Chemicals and reactions)
(6) Thermal stability and acid resistance of aluminosilicophosphate zeolites
Margulets, A. V.; Eshchenoko, L. S.; Greben'ko, N. V.; Pechkovskii; V. V.
Beloruss. Tekhnol. Inst.
Minsk, USSR
Izv. Akad. Nauk SSSR, Neorg. Mater., 22(11), 1878-82 66-3 (Surface Chemistry and Colloids)

Suitable borosilicates are exemplified by the following articles:
(1) Catalytic and acidic properties of boron pentasil zeolites
Coudurier, G.; Vedrine, J. C.
Inst. Rech. Catl., CNRS
Villeurbanne F 69626, Fr.
Stud. Surf. Sci. Catal., 28 (New Dev. Zeolite Sci. Technol.), 643-52
67-1 (Catalysis, Reaction Kinetics, and Inorganic Reaction Mechanisms)
(2) Quantum mechanical calculation on molecular sieves.
1. Properties of the Si-O-T (T si, Al, B) bridge in zeolites
Derouane, E. G.; Fripiat, J. G.
Cent. Res. Lab., Movil Res. and Dev. Corp.
Princeton, NJ 08540, USA
J. Phys. Cehm., 91(1), 145-8
(3) Acidity and catalytic activity for methanol transformation over modified borosilicate and aluminosilicate zeolites
Hegde, S. G.; Chandwadkar, A. J.
Natl. Chem. Lab.
Poona 411 008, India
Adv. Catal., [Proc.—Natl. Symp. Catal.], 7th, 163-9. Edited by: Prasada Rao, T.S.R. Wiley: New York
51-11 (Fossil Fuels, Derivatives, and Related Products)

The aluminophosphate, silicoaluminophosphate and borosilicate molecular sieves will have a channel size intermediate between 5.5×5.5 and 4.5×4.5A but excluding 4.5×4.5A as shown in Table 1.

The following Table I demonstrates the correct channel size dimensions of the molecular sieve versus other sieves which will not perform with the same adsorption characteristics as a ferrieritesized molecular sieve.

TABLE I

| Molecular Sieve | Channel Dimensions (A) | Size |
|---|---|---|
| chabazite | 3.9 × 4.1 | TOO SMALL |
| zeolite A | 3.9 × 4.1 | TOO SMALL |
| erionite | 3.6 × 5.2 | TOO SMALL |
| Ca—5A | 4.5 × 4.5 | TOO SMALL |
| ferrierite | 4.5 × 5.5 | CORRECT SIZE |
| ZSM-5 | 5.4 × 5.6 | TOO LARGE |
| offretite | 6.0 × 6.0 | TOO LARGE |
| mordenite | 6.7 × 7.0 | TOO LARGE |
| omega | 7.4 × 7.4 | TOO LARGE |
| Y zeolite | 7.4 × 7.4 | TOO LARGE |

It is also feasible that the molecular sieve can comprise a large pore zeolite that has been ion exchanged with large cations to diminish the effective channel size of the sieve to within the aforementioned range of dimensions. Thus, any molecular sieve having channel dimensions intermediate those of 5.5×5.5 and 4.5×4.5A will be considered as a preliminary candidate of the select molecular sieve of this invention.

Molecular sieves that are too small in pore size do not discriminate between mono-methyl-branched $C_6$ (i.e., methylpentanes) and di-methyl-branched $C_6$ (i.e., dimethylbutanes). In fact, they exclude both which would result in the passage of only normal paraffins to the isomerization zone. Sieves that are listed as too large do not discriminate properly between normal paraffins and mono-methyel-branched plus di-methyl-branched paraffins. In fact, thy adsorb all of these paraffins. In the event a sieve is used with too large a pore size, the di-methyl-branched paraffins would be present in the feed to isomerization which, at best, means that a species already highly branched will occupy valuable reactor time or, at worst, the already highly branched species could react to a less valuable isomer. Only sieves between, and not including, the pore sizes of the sieves of calcium-5A and ZSM-5 selectively discriminate to accommodate mono-methyl-branched paraffins and normal paraffins while excluding di-methyl-branched $C_6$ paraffins. While ferrierite is the best example of such a sieve, this invention should not be limited to ferrierite per se as the only species which is operable for this process.

The adsorption/desorption conditions typically utilized with the molecular sieves of this invention comprise a temperature of from about 75° C. to about 400° C. and a pressure of from about 2 bar to about $\Delta$bar. The adsorption and desorption conditions are very similar to the conditions present in the separation sieve frequently operated downstream of isomerization. Specific desorbents utilized in order to extract the desired trapped normal paraffins and mono-methyl paraffins to collect and transmit those materials to the isomerization zone will preferably be hydrogen, which does not effect the isomerization of the paraffinic materials in the isomerization zone.

The paraffinic feed material is passed through an isomerization reactor having an isomerization catalyst therein. The isomerization catalyst is preferably a zeolite with a catalytic metal disposed thereon. Exemplary of such a catalyst is mordenite with platinum present in a range of 0.005 wt% to 10.0 wt% with a preferred range being from 0.2 to 0.4 wt% Other zeolite molecular sieves are also viable which have a silica to alumina molar ratio of greater than 3 and less than 60 and preferably less than 15. The zeolite molecular sieves may have many polyvalent metal cations exchanged with the sieve, such as those of the alkali metals or alkaline earth metals. The catalytic metals associated with the isomerization function are preferably noble metals from Group VIII of the Periodic Table of elements. These can be exemplified by such metals as platinum, palladium, osmium, ruthenium, etc. The isomerization catalyst can be present per se or it may be mixed with a binder material. Other equivalent isomerization catalysts can be utilized within the confines of this invention; however, the mordenite-Group VIII metal catalyst is preferred. For example, a faujasite molecular sieve may be utilized but has poorer selectivity than mordenite.

The isomerization conditions present in the isomerization zone are those selected to maximize the conversion of normal paraffins and mono-methyl-paraffins to di-methyl-branched paraffins. This type of isomerization is favored in the vapor phase with a fixed bed of isomerization catalyst. Typical operating temperatures include from 200 to 400° C. with pressures of about 10 to 40 bar. The isomerization process, which is limited in octane upgrading by thermodynamic equilibria, is frequently measured at 10 points. Even at these select conditions, the effluent from the isomerization reactor will still contain substantial (e.g. 20 to 30 wt%) normal paraffins and mono-methyl-branched paraffins which are unreacted or partially reacted due to the aforementioned equilibrium.

One of the advantageous aspects of this invention is the fact that the di-methyl-branched paraffins are not passed to the isomerization zone. The isomerization reaction has a chemical equilibrium. The exclusion of the dimethyl paraffins from the isomerization zone is advantageous for maximizing the quantity of di-methyl paraffins produced during isomerization while at the same time, reducing the number of normal paraffins which remain unisomerized in the isomerization zone effluent stream. After isomerization, the isomerization zone feed stream will contain unisomerized normal paraffins, mono-methyl paraffins and di-branched paraffins.

The isomerization zone effluent stream, after suitable removal of light ends which are sometimes generated during isomerization, can be sent directly to the gasoline pool or it can be passed to a separation zone which will preferably comprise from three to eight adsorbent beds which can be modified to operate in an adsorption/desorption mode as exemplified in U.S. Pat. No. 4,210,771, all of the teachings of which, in regard to the function of adsorption/desorption are herein incorporated by reference. This separation zone will contain a multiple number of one type of separatory sieve which can be exemplified by such sieves as a calcium-5A sieve or a ferrierite sieve. The calcium-5A sieve is capable of adsorbing virtually no methylpentane (nor dimethylbutane) and thus will recycle only normal paraffins to complete isomerization.

In contrast to the calcium 5-A sieve, a molecular sieve, such as used in the preliminary separatory sieve upstream of the isomerization can be utilized to form a recycle stream of mono-methyl-branched paraffins and normal paraffins. The aforementioned examples of the particular molecular sieves, having a pore size of 5.5×5.5 and 4.5×4.5A, are exemplary of the molecular sieve which can be utilized to separate the isomerization zone effluent stream to form the advantageous mono-methyl-branched paraffin and normal paraffin recycle stream. It is not necessary that all of the normal paraffins (in the case of a calcium-5A sieve) or all of the mono-methyl-branched paraffins and normal paraffins (in the case of a ferrierite-sized molecular sieve) be recycled to isomerization. However, for economic purposes it is sometimes beneficial that all paraffins containing branching with less than two alkyl moieties be recycled until an equilibrium is reached maximizing the quantity of di-methyl branched paraffins.

In this later process, two gasoline blending component streams are acquired. First, the material which will elute through the preliminary sieve upstream of isomerization will contain very high octane paraffins in addition to any aromatics and naphthenes present in the feed. The second gasoline blending component will be derived downstream of the separator sieve which acts on the isomerization zone effluent. These two isomerate streams can be combined and utilized as a single blending component or they can be used individually.

DETAILED DESCRIPTION OF THE DRAWINGS

Figure 1:
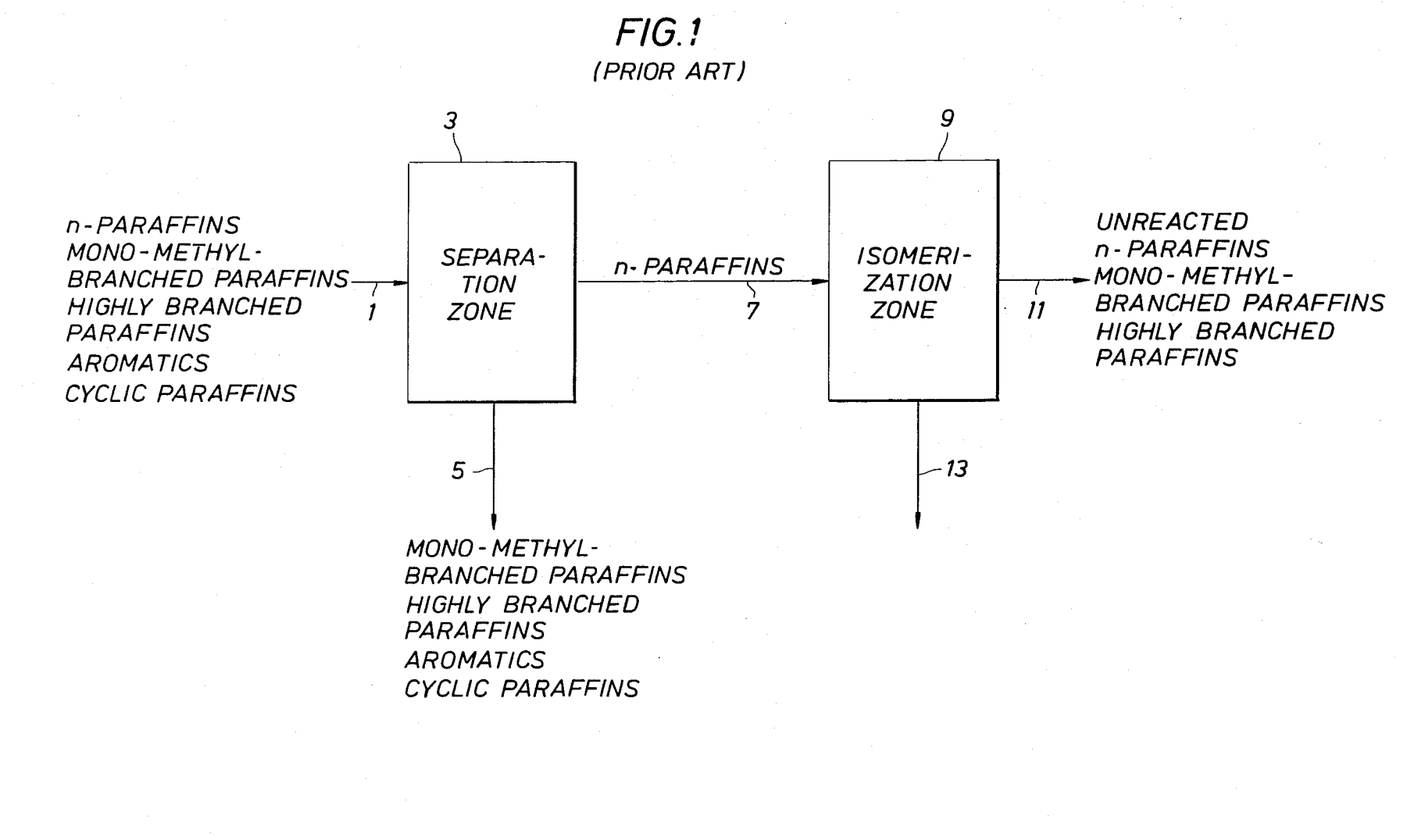
FIG. 1 is a schematic flow scheme of the process of the prior art.

In FIG. 1 a feedstream comprising a fresh feed having, for example, 4 mol% $C_1$ to $C_5$; and 93 mol% $C_6$ paraffins with small quantities of cycloparaffins, aromatics, and $C_7$+paraffins are passed through conduit 1 into a separator zone 3 having at least three and preferably up to 8 adsorbent beds of a molecular sieve such as a calcium-5A zeolite sieve to separate feed constituents. The calcium-5A sieve will entrap or absorb normal paraffins while allowing mono-methyl-branched paraffins and other branched paraffins to pass through the separation zone and be recovered in conduit 5 as a gasoline blending component. After applicable desorption with means not shown, a normal paraffin stream in conduit 7 is withdrawn from the separatory zone 3 and passed to isomerization zone 9. This zone is maintained at conditions selected to maximize the degree of branching of the product stream 11. A typical isomerization catalyst as described at Column 5 of U.S. Pat. No. 4,210,771 can be present in this prior art process. If desirable, a vented hydrogen or light hydrocarbon gas stream can be removed from the isomerization zone in conduit 13. An effluent stream from isomerization zone 9 is removed in conduit 11 containing normal paraffins, mono-methyl-branched paraffins and more highly branched paraffins (e.g. ethylpentane, dimethylbutane etc.).

Figure 2:
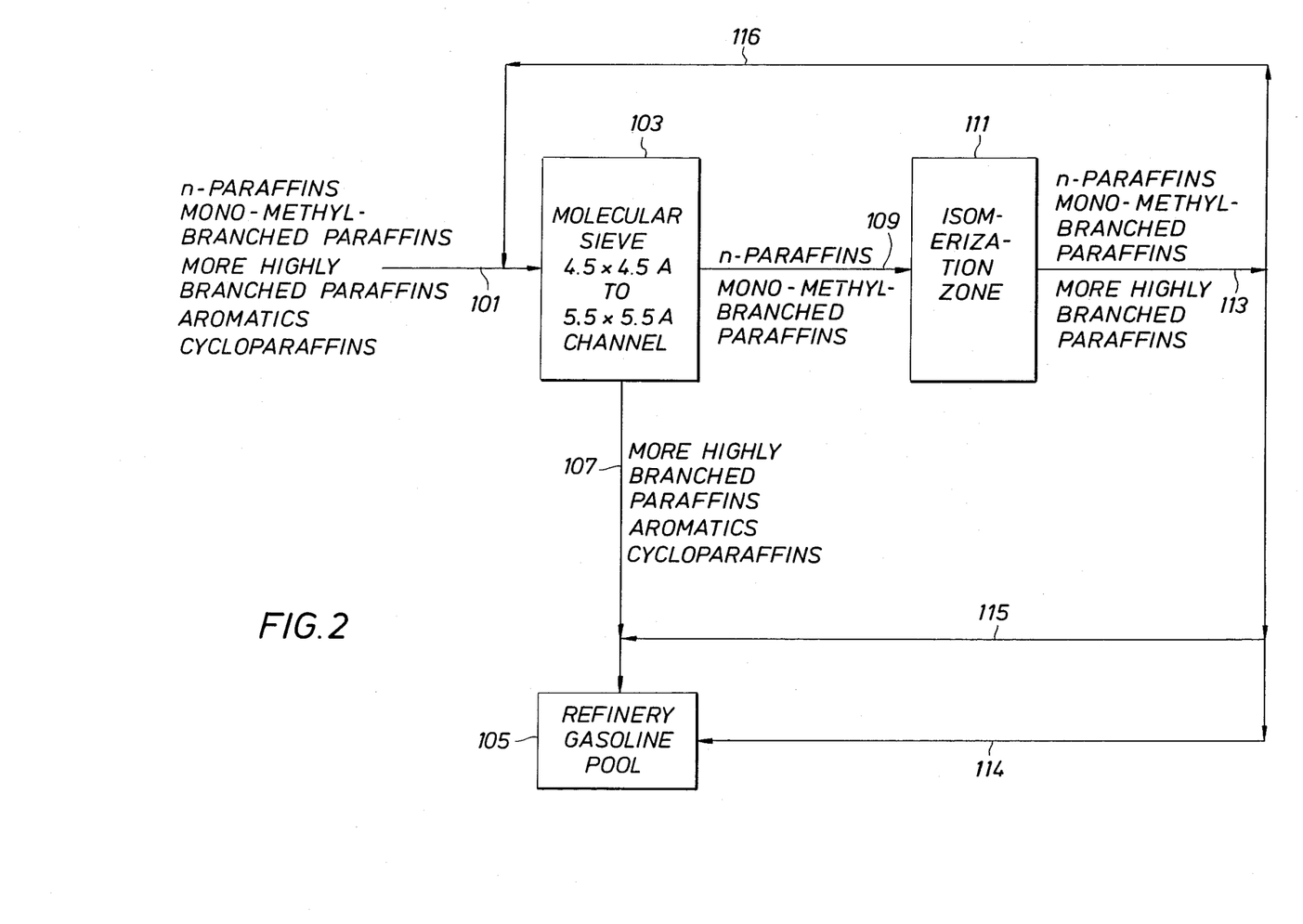
FIGS. 2-5 are schematic flow schemes of the novel process of this invention utilizing a molecular sieve upstream of isomerization.

FIG. 2 demonstrates the use of this process on a similar type of hydrocarbon feed stream as exemplified in FIG. 1 with the advantage of use of the select molecular sieve of the instant invention upstream of isomerization. The feed stream in conduit 101 is passed to sieve separation zone 103 containing a molecular sieve having channel dimensions intermediate 5.5×5.5 and 4.5×4.5A. Said molecular sieve may comprise ferrierite and may be produced by any known ferrierite synthesis method as exemplified in U.S. Pat. Nos. 4,016,245 and 4,251,499, and "Selectivity Induced by the Void Structure of Zeolite Beta and Ferrierite in Hydroconversion Hydroconversion of n-Decane," pages 115–129, J. A. Martens. All of these three publications are hereby incorporated by reference.

The molecular sieve in zone 103 adsorbs normal paraffins and mono-methyl-branched paraffins. More highly branched paraffins and any aromatic and naphthene compounds are not adsorbed but are permitted to elute through the sieve and are collected in refinery gasoline pool 105 by means of conduit 107 as the first gasoline blending stream from the feed stream separation zone of this invention. This stream has an octane value which would be diminished if isomerized. After proper desorption, with a desorbent such as hydrogen or stream, normal paraffins and mono-methyl-branched paraffins are withdrawn from sieve 103 in conduit 109 and passed to isomerization zone 111 wherein the normal paraffins are isomerized to both mono-methyl paraffins and more highly branched paraffins while the mono-methyl branched paraffins are isomerized to more highly branched paraffins. Because of the equilibrium existing in the isomerization zone, only a certain percentage of the isomerization zone effluent in conduit 113 comprises highly branched paraffins with the remainder comprising mostly mono-methyl-branched paraffins and unisomerized normal paraffins. The isomerization zone effluent in conduit 113 can be transferred in any of several ways, in whole or in part. It can be transmitted via 114 directly to the refinery gasoline pool. It can be transmitted via conduit 115 to commingle with the feed separation zone effluent of conduit 107. It can also be transmitted via conduit 116 back to feed conduit 101. Or, finally, it can undergo additional segregation. Both the mono-methyl-branched paraffins and the more highly branched paraffins can be recovered as high octane isomerate material.

Figure 3:
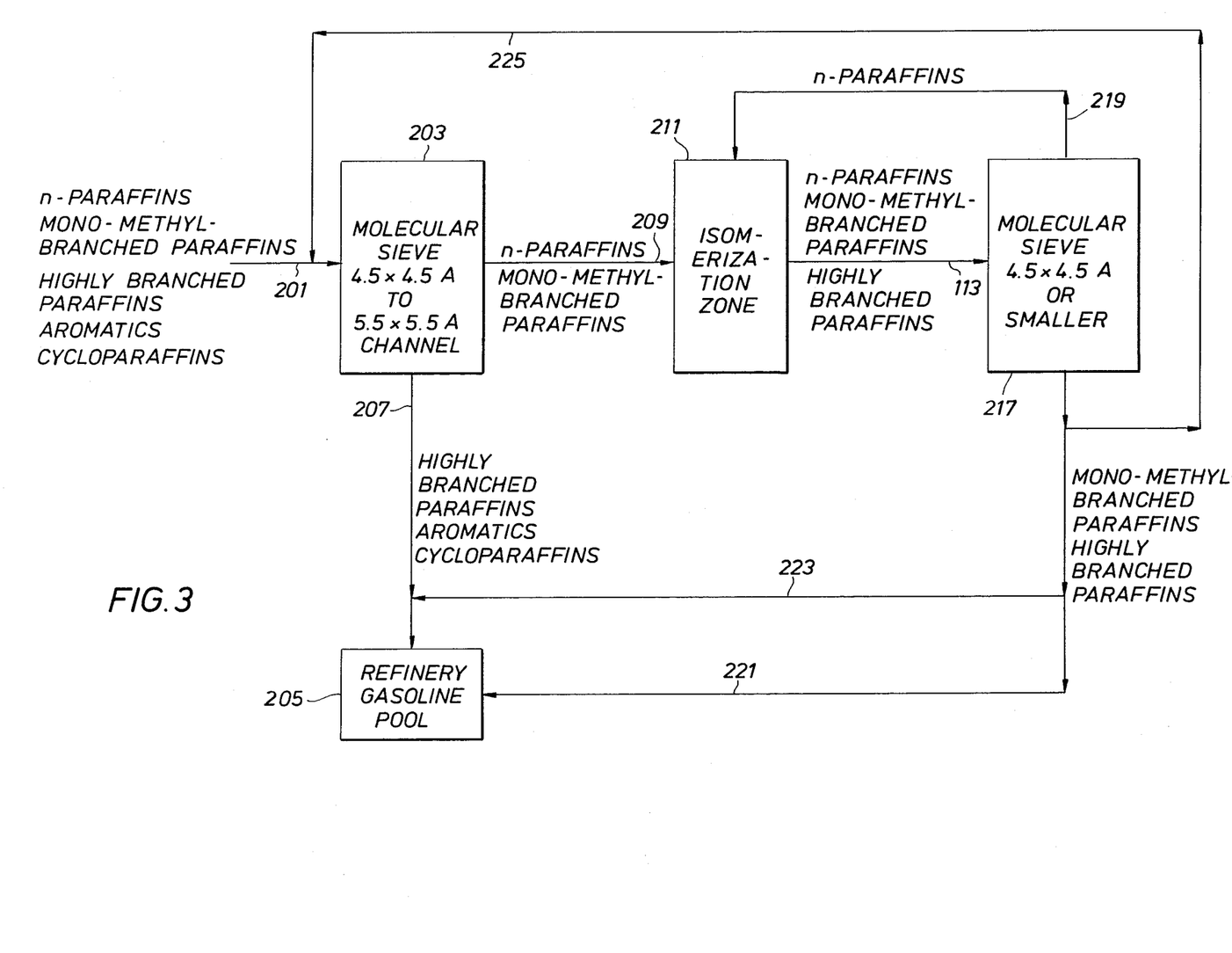

FIG. 3 shows a preferred embodiment of this process invention. A hydrocarbon feed stream in conduit 201 is passed to a select molecular sieve as described in FIG. 2, item 103. The refinery gasoline pool 205 is provided with high octane components in 207 very similar to stream 107 of FIG. 2. Normal and mono-methyl-branched paraffins are captured by the molecular sieve in separation zone 203 and passed to isomerization zone 211 via conduit 209. A second separatory sieve 217 operates to separate normal paraffins from the mono-methyl-branched paraffins and said more highly branched paraffins. A calcium-5A zeolite will function adequately to segregate said mono-methyl-branched paraffins from normal paraffins. In this embodiment mostly normal paraffins will be recycled to isomerization zone 211 by means of conduit 219. The unadsorbed mono-methyl-branched paraffins together with the unadsorbed more highly branched paraffins can pass in whole or in part through conduit 221 directly to the gasoline pool, or through conduit 223 to commingle with the feed separation zone effluent, or passed via conduit 25 back to feed conduit 201.

Figure 4:
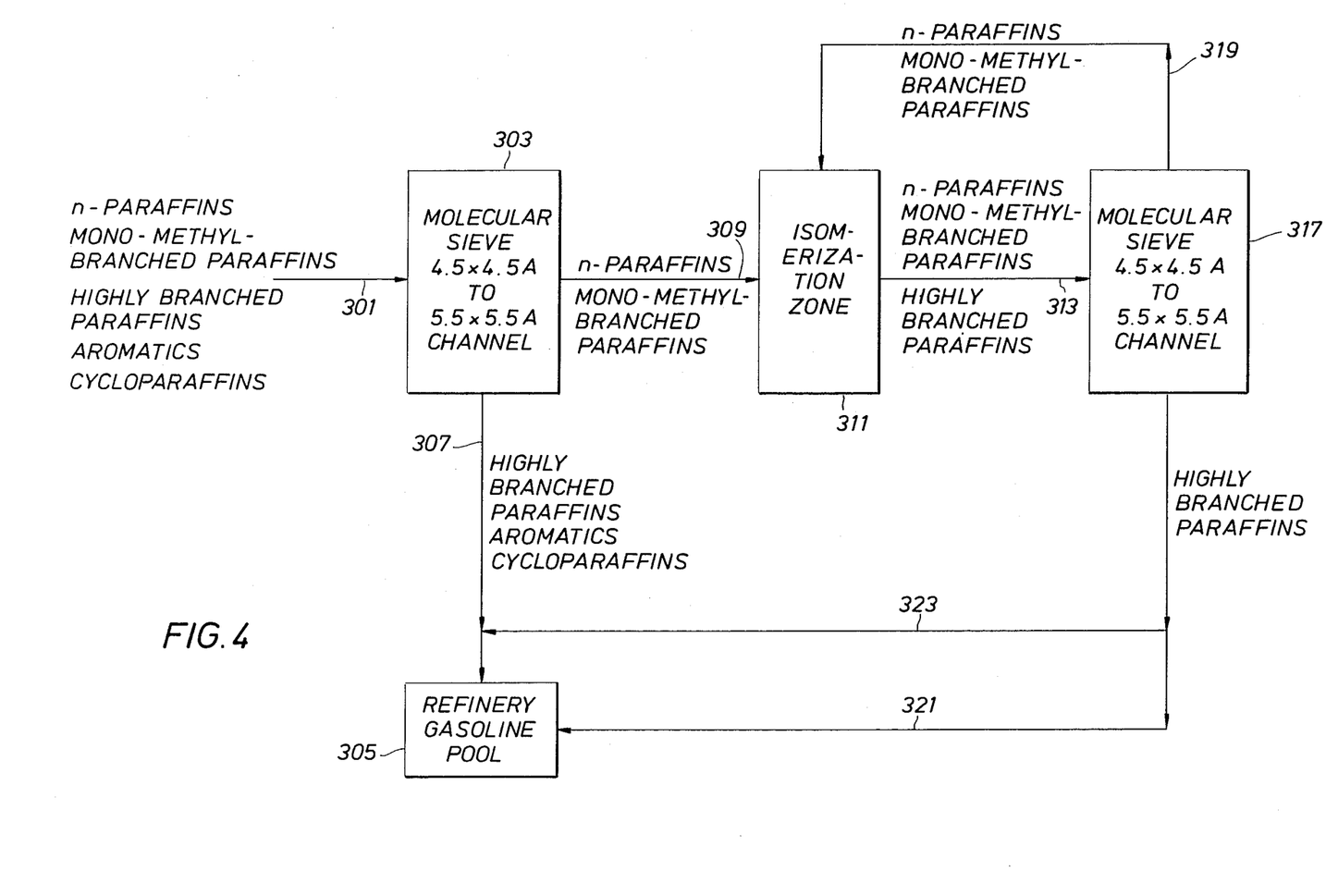

FIG. 4 shows another preferred embodiment of this process invention. A hydrocarbon feed stream in conduit 301, similar in make-up to stream 101 of FIG. 2, is passed to a select molecular sieve 303 as described in FIG. 2, item 103. The refinery gasoline pool 305 is provided with high octane components in 307, very similar to stream 107 of FIG. 2. Normal paraffins and mono-methyl-branched paraffins are captured by the molecular sieve in separation zone 303 and passed to isomerization zone 311 via conduit 309. A second separation zone 317 contains a molecular sieve similar to that contained in zone 303. It is preferred that this molecular sieve is ferrierite.

Where a ferrierite is located in separation zone 317, more highly branched paraffins are not adsorbed and are withdrawn from separation zone 317 and are passed in whole or in part via conduit 321 direct to the refinery gasoline pool or passed via conduit 323 to commingle with feed separation zone effluent. After proper desorption, the normal and mono-methyl paraffins are removed from separation zone 317 and at least a portion recycled to isomerization zone 311 by means of conduit 319.

Figure 5:
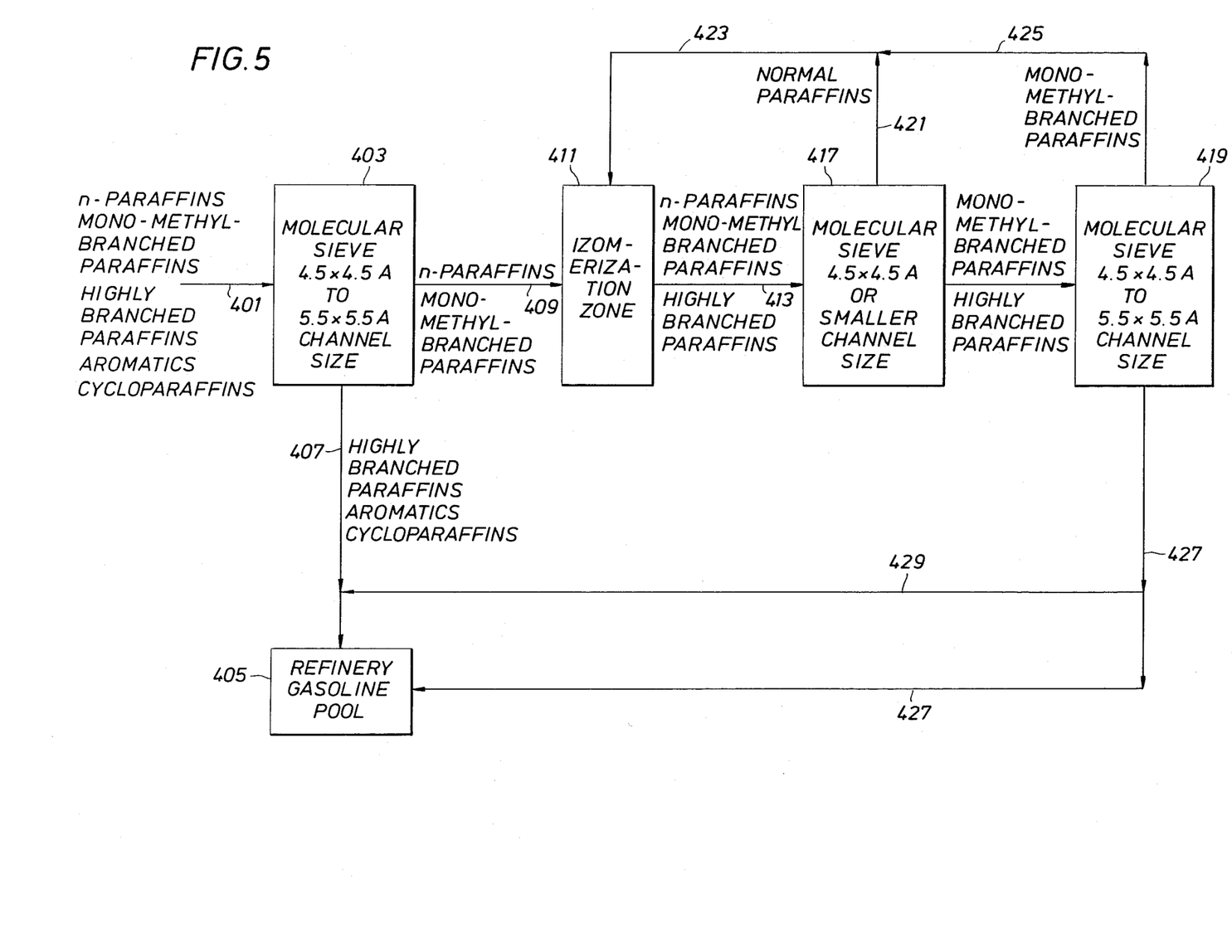

FIG. 5 shows yet another preferred embodiment of this process invention. A hydrocarbon stream in conduit 401 (similar to stream 101) is passed to a select molecular sieve 403, as described in FIG. 2, item 103. The refinery gasoline pool 405 is provided with high octane components in 407, very similar to stream 107 of FIG. 2. Normal and mono-methyl-branched paraffins are captured by the molecular sieve in separation zone 403 and passed to isomerization zone 411 via conduit 409. Due to capacity differences intrinsic to different molecular sieve structures, a first product separation zone 417, containing a normal paraffin adsorbing sieve (Ca5A, for example), is followed by a second product separation zone 419 containing a mono-methyl-branched-paraffin adsorbing sieve (ferrierite, for example.) Both can be employed together for an overall reduction in volume of molecular sieve required to effect the separation of normal paraffins and mono-methyl-branched paraffins from more hghly branched paraffins. It is also within the scope of the instant preferred process invention (FIG. 5) that the dual sieve system 417–419 comprises a stacked bed within a unitary vessel.

Normal paraffins can be recycled from sieve 417 to isomerization zone 411 by means of 421–423. At the same time or at a different time, mono-methyl-branched paraffins can be recycled from sieve 419 to isomerization 411 by means of 425–423. More highly branched paraffins are added to the gasoline pool 405 by stream 427 or a slip stream 429 may be taken off stream 427 and passed to stream 407. In any event, streams 407, 427 and 429 all contribute to the high octane gasoline pool of this process invention.

ILLUSTRATIVE EMBODIMENTS

The instant examples are given as examples of the instant process and the benefit achieved by situating the select molecular sieve before isomerization of the hydrocarbonaceous material.

EXAMPLE 1

In this example, sorption capacities of sodium ferrierite, calcium-5A and sodium ZSM-5 sieves were determined in regard to normal hexane, 3-methylpentane and 2,3-dimethylbutane. The particular denoted zeolite was placed on a pan in a Cahn balance, the sample chamber was evacuated, and heated to 550° C. for one hour. The particular zeolite was thus dried and following drying was cooled to 105° C. At this time, hydrocarbon vapors were admitted to the evacuated chamber to a level of 100 torr. Weight changes due to the adsorption of hydrocarbon into the zeolite were recorded. An exposure time of three hours was allowed for the branched hydrocarbons to approach equilibrium weight, whereas an exposure time of only one half hour was required for normal hexane. The results of this adsorption are shown in Table 2. Each combination of zeolite plus solvent was subjected to at least three separate determinations. Listed in the Table are results of individual determinations, as well as means and standard deviation values for each set of determinations.

TABLE 2

| Hydrocarbon | Weight of HC Adsorbed (mg/g) | | |
|---|---|---|---|
| | Ca—5A | Na—Ferrierite | Na—ZSM-5 |
| 2,3-Dimethylbutane | 1.6 | 2.1 | 59.4 |
| | 1.3 | 1.7 | 59.7 |
| | 1.9 | 1.9 | 61.1 |
| | 2.4 | 1.8 | — |
| MEAN + STD DEV: | 1.8 ± 0.4 | 1.9 ± 0.1 | 60.0 ± 0.9 |
| 3-Methylpentane | 1.7 | 19.4 | 56.5 |
| | 1.9 | 19.6 | 63.9 |
| | 2.0 | 18.4 | 62.3 |
| | 1.5 | — | — |
| | 1.2 | — | — |
| MEAN + STD DEV: | 1.7 ± 0.3 | 19.2 ± 0.5 | 60.9 ± 3.8 |
| n-Hexane | 92.3 | 55.4 | 111.9 |
| | 90.1 | 54.5 | 105.4 |
| | 100.7 | 53.9 | 106.7 |
| | 99.3 | 56.7 | — |
| MEAN + STD DEV: | 95.6 ± 4.5 | 55.2 ± 1.0 | 107.9 ± 3.4 |

The sorption capacities are reported as weight gain in the sieve relative to the dry weight of the pure zeolite. As shown in Table 2, the calcium-5A zeolite adsorbed very little branched hydrocarbon. The ratio of 3-methylpentane/normal hexane sorption capacities is 0.018. In contrast, sodium ferrierite adsorbed little dimethylbutane but adsorbed a substantial amount of 3-methylpentane. The ratio of the 3-methylpentane/normal hexane sorption capacity is about 20 times greater for the sodium ferrierite than for calcium-5A zeolite. The sodium ZSM-5 sieve adsorbed virtually identical amounts of the mono- and di-branched isomers. Thus, the aforedescribed sodium ferrierite has the capability to effect a separation between 3-methylpentane and 2,3-dimethylbutane upstream of isomerization by capturing 3-methylpentane while permitting 2,3-dimethylbutane to elute and, thereby, has the capability to preserve the octane quality of the higher octane paraffin. Moreover, the sodium ferrierite treatment of a feed stream containing the aforementioned components will permit the capture (adsorption) of both 3-methylpentane and normal hexane which can then be desorbed and passed to an isomerization zone for their ultimate conversion to 2,3-dimethybutane.

EXAMPLE 2

The sorption capacities of hydrogen ferrierite towards the same three hydrocarbons were determined and are presented in Table 3. These data clearly show the comparison of the hydrogen ferrierite versus the calcium-5A zeolite. The ratio of 3-methylpentane/normal hexane sorption for the hydrogen ferrierite is about 25 times greater than that for the calcium-5A sieve. A comparison of the sodium ferrierite and hydrogen ferrierite, i.e., see Tables 2 and 3, underscores the discovery that appropriately sized molecular sieves can be very advantageous when placed upstream of an isomerization zone to separate out high octane hydrocarbons prior to isomerization.

TABLE 3

| Hydrocarbon | H—Ferrierite | Ca—5A |
|---|---|---|
| 2,3-Dimethylbutane | 3.6 | 1.6 |
| | 3.3 | 1.3 |
| | 3.2 | 1.9 |
| | 3.1 | 2.4 |
| MEAN + STD DEV: | 3.3 ± 0.2 | 1.8 ± 0.4 |
| 3-Methylpentane | 28.8 | 1.7 |
| | 28.6 | 1.9 |
| | 27.1 | 2.0 |
| | | 1.5 |
| | 27.4 | 1.2 |
| MEAN + STD DEV: | 28.0 ± 0.8 | 1.7 ± 0.3 |
| n-Hexane | 56.5 | 92.3 |
| | | 90.1 |
| | | 100.7 |
| | | 99.3 |
| MEAN + STD DEV: | 56.5 | 95.6 ± 4.5 |

EXAMPLE 3

A sample of ammonium ferrierite was tableted to 14–45 mesh and placed in a glass tube. The glass tube was placed in a tube furnace under a flow of nitrogen and heated to 500° C. for 2 hours to expel ammonia and thus produce the hydrogen form of ferrierite. Under the same nitrogen flow, the molecular sieve was cooled to room temperature while the nitrogen flow was diverted through a gas saturation tower containing a mixture of normal hexane, 3-methylpentane and 2,3-dimethylbutane. The molecular sieves were exposed to hydrocarboncontaining streams of nitrogen for 1 hour. Samples of the hydrocarbon reservoir were taken at the beginning and at the end of the gas saturation period. The purpose of sampling both at the start and at the end of the experiment was to verify that the ratio of hydrocarbons remained essentially constant throughout the experiment. A portion of the hydrocarbon-containing vapor stream was diverted directly through a cold finger that was immersed in a dry ice/acetone bath to collect a sample of the actual hydrocarbon vapors.

Following exposure to these vapors, the hydrocarbon-saturated ferrierite sample was removed from the glass tube and placed on a vacuum line. The sample was evacuated to below 1 torr through a cold finger immersed in liquid nitrogen. The sample was heated to 40° C. and the sorbed hydrocarbon was quantitatively removed from the zeolite. It was experimentally determined that this first trapping was quantitative. The results of the adsorption were analyzed by gas chromatography and are shown in Table 4.

TABLE 4

| | Competitive Sorption of Hexane Isomers By H—Ferrierite | | |
|---|---|---|---|
| Sample | % w 2,3-DMB | % w 3-MP | % w n-hexane |
| Gas saturation tower contents at start of experiment | 34.7 | 37.1 | 28.2 |
| Gas saturation tower contents at end of experiment | 26.7 | 36.8 | 36.5 |
| Gaseous hydrocarbon stream | 41.7 | 36.3 | 22.0 |
| Hydrocarbon adsorbed by H—ferrierite | 1.4 | 17.2 | 81.4 |

As shown in Table 4, very little dimethylbutane will enter the pores of the molecular sieve exemplified by hydrogen ferrierite. This is very advantageous because the higher octane dimethylbutane avoids capture (adsorption) and is thereby preserved upstream of isomerization. A substantial amount of mono-methylpentane will be captured by the sieve and can then be recovered and passed to the isomerization zone for its conversion to 2,3-dimethyl-butane. In this manner, the unconverted or partially converted paraffins in the recycle stream (exemplified by conduit 116 in FIG. 2) will be readily isomerized to exhaustion in comparison to a process operated without the molecular sieve of the instant invention upstream of the isomerization zone.

What we claim as our invention is:

1. A process for the isomerization of paraffins from a mixed hydrocarbon stream comprising normal paraffins, mono-methyl-branched paraffins, di-methyl-branched paraffins, said process comprising:
   (a) passing said mixed hydrocarbon stream to a feed separation zone comprising a shape-selective separatory molecular sieve having an intermediate pore size of 5.5×5.5 to 4.5×4.5A and excluding 4.5×4.5A, said pore size being sufficient to permit entry of said normal paraffins and said mono-methyl-branched paraffins but restrictive to prohibit entry of di-branched paraffins;
   (b) separating, in said feed separation zone, at separation conditions, by means of said shape-selective separatory sieve, said di-branched paraffins from said normal paraffins and mono-methyl- branched paraffins;
   (c) recovering from said feed separation zone a feed separation zone effluent stream comprising said di-branched paraffins;
   (d) recovering from said feed separation zone an isomerization feed stream comprising said normal paraffins and said monomethyl-branched paraffins;
   (e) passing at least a portion of said isomerization feed stream to an isomerization zone maintained at isomerization conditions and containing an isomerization catalyst to produce an isomerization zone effluent stream comprising di-branched paraffins, mono-methylbranched paraffins and normal paraffins.

2. The process of claim 1 wherein at least a portion of said isomerization zone effluent stream is passed to a product separation zone containing a select shape-selective zeolite to separate, at separation conditions, said di-branched paraffins and said mono-methyl branched paraffins from said normal paraffins of said isomerization effluent stream and to form an isomerization zone recycle stream comprising normal paraffins; and recovering at least a portion of said di-branched paraffins and mono-methyl-branched paraffins as a product separation zone effluent stream.

3. The process of claim 1 wherein said isomerization conditions include a temperature of 200° C. to 400° C. and a pressure of from about 10 bar to about 40 bar.

4. The process of claim 1 wherein said isomerization catalyst comprises an aluminosilicate having a Group VIII metal deposited therewith.

5. The process of claim 4 wherein said aluminosilicate is mordenite and said Group VIII metal is platinum.

6. The process of claim 5 wherein said platinum is present in a weight concentration of from about 0.2 to about 0.4 wt%.

7. The process of claim 5 wherein said mordenite has associated therewith an inorganic binder.

8. The process of claim 1 wherein said shape-selective molecular sieve of said feed separation zone comprises synthetic ferrierite.

9. The process of claim 1 wherein said aluminosilicate comprises natural ferrierite.

10. The process of claim 1 wherein said shape-selective molecular sieve is selected from the group consisting of tectosilicates, aluminophosphates and silicoaluminophosphates.

11. The process of claim 10 wherein said tectosilicates are selected from the group consisting of aluminosilicates and borosilicates.

12. The process of claim 1 wherein said shape-selective separatory sieve of said feed separation zone comprises ferrierite having cations exchanged therein selected from the group consisting of an alkali metal, alkaline earth metal and transition metal cations.

13. The process of claim 1 wherein said separation conditions include a temperature of from about 75° C. to about 400° C. and a pressure of from about 2 bar to about 42 bar.

14. The process of claim 1 wherein said di-branched paraffins recovered in step (c) comprise 2,3-di-methyl-butane and wherein said mono-methyl-branched paraffins recovered in step (d) comprise 3-methyl pentane.

15. The process of claim 2 wherein said feed separation zone effluent stream and said product separation zone effluent stream are admixed before blending with a gasoline range hydrocarbon.

16. The process of claim 2 wherein said feed separation zone effluent stream and said product separation zone effluent stream are combined and wherein said combined stream comprises an isomerate gasoline blending stream containing a predominant amount of di-methyl-branched paraffins and a minor amount of said mono-methyl-branched paraffins.

17. The process of claim 1 wherein said mixed hydrocarbon feed stream contains aromatic and naphthenic hydrocarbons and wherein said shape-selective separatory sieve is restrictive to prohibit entry of said aromatic and naphthenic hydrocarbons and wherein said aromatic and naphthenic hydrocarbons are recovered with said feed separation zone effluent stream.

18. The process of claim 2 wherein said product separation zone comprises a calcium 5A zeolite sufficient to permit adsorption of said normal paraffins and restrictive to adsorption of said mono-methyl-branched paraffins and di-branched paraffins.

19. The process of claim 2 wherein said product separation zone effluent stream is passed to a subsequent product separation zone containing a shape-selective molecular sieve to separate, at separation conditions, di-branched paraffins from mono-methyl branched paraffins and to form an isomerization zone recycle stream comprising mono-methyl branched paraffins and recovering at least a portion of said di-branched paraffins as a subsequent product separation zone effluent stream.

20. The process of claim 19 wherein said select shape-selective molecular sieve of said subsequent product separation zone has a pore diameter between 4.5×4.5A and 5.5×5.5A and excluding 4.5×4.5A.

21. The process of claim 20 wherein said molecular sieve comprises ferrierite.

22. The process of claim 1 wherein at least a portion of said isomerization zone effluent stream is passed to a product separation zone comprising a select shape-selective zeolite to separate, at separation conditions, said di-branched paraffins from said mono-methyl branched paraffins and normal paraffins and to form an isomerization zone recycle stream comprising normal paraffins and mono-methyl branched paraffins; and recovering at least a portion of said di-branched paraffins as a product effluent stream.

23. The process of claim 22 wherein said select shape-selective zeolite of said product separation zone has a pore diameter between 4.5×4.5A and 5.5×5.5A and excluding 4.5×4.5A.

24. The process of claim 22 wherein said shape-selective zeolite comprises ferrierite.

25. The process of claim 2 wherein said product separation zone effluent stream comprising di-branched paraffins and mono-methyl branched paraffins is separated by a separation means to provide a subsequent product effluent stream comprising di-branched paraffins and an isomerization zone recycle stream comprising mono-methyl branched paraffins.

26. The process of claim 1 wherein at least a portion of said isomerization zone effluent stream is recycled to said feed separation zone.

27. The process of claim 1 wherein said isomerization zone effluent streams is separated to yield an issomerization zone recycle stream comprising normal paraffins which are recycled to said isomerization zone.

28. A process for the preparation of an isomerate from a hydrocarbon feed stream mixture containing normal hexane, methyl pentanes and di-methyl butane which comprises: (1) passing said feed stream to a feed separation zone containing a separatory shape-selective molecular sieve having an intermediate pore size of 5.5×5.5 to 4.5×4.5A and excluding 4.5×4.5A, said shape-selective molecular sieve being effective to permit entry of said normal hexane and mono-methylpentanes and restrictive to prohibit entry of said dimethyl butane and to thereby separate said dimethyl butane from said normal hexane and mono-methylpentanes; (2) recovering said dimethyl butanes as a feed separation zone effluent stream; (3) recovering adsorbed normal hexane and mono-methylpentanes and passing said normal hexane and mono-methylpentane to an isomerization zone and isomerizing, at isomerization conditions, in the presence of an isomerization catalyst said normal hexane to methyl pentanes and dimethyl butane; and isomerizing said mono-methylpentanes to dimethyl butane, and (4) forming an isomerization effluent isomerate stream comprising unisomerized normal hexane, mono-methylpentanes and dimethyl butane.

29. The process of claim 28 wherein at least a portion of said isomerization effluent stream is passed to a product separation zone containing a shape-selective separatory molecular sieve with a pore size equal to or smaller than 4.5×4.5A thereby permitting adsorption of said normal hexane while eluting said methylpentanes and said dimethyl butane, wherein said adsorbed normal hexane is recovered and at least a portion thereof is recycled to said isomerization zone and recovering said mono-methylpentanes and dimethyl butanes as a product separation zone isomerate effluent.

30. The process of claim 28 wherein said shape-selective molecular sieve is selected from the group consisting of tectosilicates, aluminophosphates and silicoaluminophosphates.

31. The process of claim 29 wherein said product separation zone isomerate effluent comprising dimethylbutanes and mono-methylpentanes is passed to said feed separation zone.

32. The process of claim 30 wherein said tectosilicates comprise aluminosilicates and borosilicates.

33. The process of claim 32 wherein said aluminosilicate comprises ferrierite.

34. The process of claim 28 wherein said isomerization catalyst comprises a mordenite aluminosilicate having platinum dispersed thereon.

35. The process of claim 34 wherein said platinum is present in a weight content of from about 0.005 wt% to about 10.0 wt%.

36. The process of claim 28 wherein said isomerization catalyst comprises a Y faujausite sieve having 0.2 to 1.4 wt% platinum dispersed thereon.

37. The process of claim 28 wherein said feed stream is comprised of normal hexane, methyl pentanes, dimethyl butane, aromatics and naphthenes, wherein said aromatics and naphthenes are not adsorbed in said separatory shape selective molecular sieve and wherein said aromatics and naphthenes are recovered in said feed separation zone effluent stream.

38. The process of claim 29 wherein said feed separation effluent stream is comprised of dimethyl butanes and said product separation zone isomerate effluent is comprised of methyl pentanes and dimethyl butanes, wherein said streams are combined to form a combined isomerate gasoline blending component.

39. The process of claim 38 wherein said dimethyl butane is 2,3-dimethyl butane.

40. The process of claim 29 wherein said shape-selective separatory molecular sieve in said product separation zone comprises calcium 5A.

41. The process of claim 29 wherein said first product separation zone isomerate effluent stream is passed to a product separation zone containing a shape-selective molecular sieve to separate, at separation conditions, mono-methylpentanes from dimethylbutane, to form an isomerization zone recycle stream comprising mono-methyl pentanes and wherein said dimethylbutanes are recovered as a subsequent product separation zone isomerate effluent stream.

42. The process of claim 41 wherein both said feed separation zone and said product separation zone contains a ferrierite zeolite, wherein both said zones are maintained at separation conditions including a temperature of from about 75° C. to about 400° C. and a pressure of from about 2 bar to about 42 bar.

43. The process of claim 41 wherein said shape-selective molecular sieve of said product separation zone has a pore diameter between 4.5×4.5A and 5.5×5.5A and excluding 4.5×4.5A.

44. The process of claim 28 wherein said effluent isomerate stream is combined with said feed separation zone effluent stream.

45. The process of claim 28 wherein said isomerization zone isomerate effluent stream comprises dimethylbutanes, mono-methylpentanes, and normal hexane, wherein at least a portion of said isomerization zone isomerate effluent stream is passed to said feed separation zone as a recycle stream.

46. The process of claim 28 wherein said isomerization zone effluent stream undergoes separation to yield an isomerization zone recycle stream comprising normal hexane which is passed to said isomerization zone to isomerize said normal hexane mono-methylpentanes and dimethylbutane.

* * * * *